Figure 1:
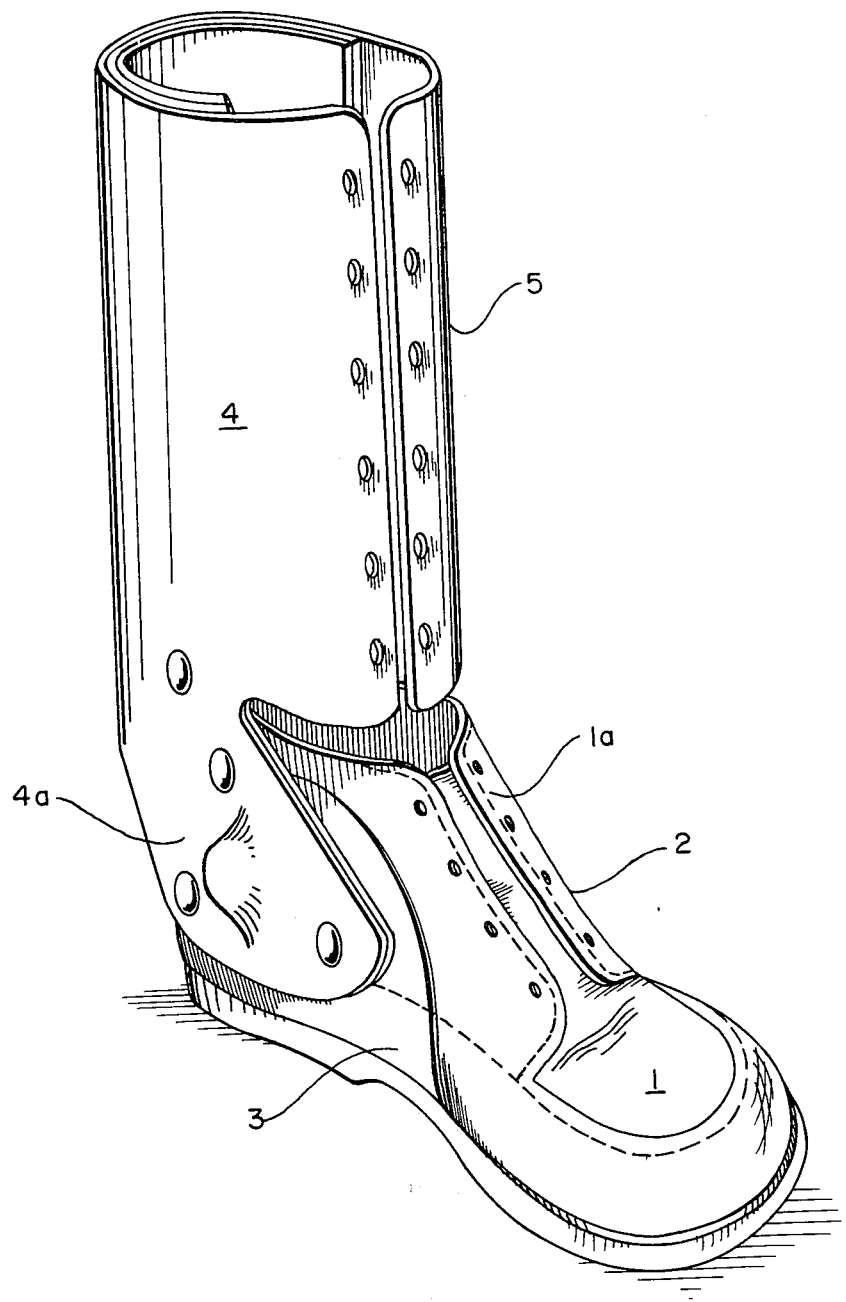

United States Patent [19]
Burke

[11] 3,948,253
[45] Apr. 6, 1976

[54] ORTHOPEDIC SHOE

[76] Inventor: Murray G. Burke, 21 Mic Mac Drive, Dartmouth, Nova Scotia, Canada

[22] Filed: Jan. 27, 1975

[21] Appl. No.: 544,501

[30] Foreign Application Priority Data
Nov. 22, 1974 Canada................................. 214438

[52] U.S. Cl. ............................................. 128/80 J
[51] Int. Cl.² .......................................... A61F 3/00
[58] Field of Search...... 128/80 J, 80 E, 80 R, 80 F; 36/2.5 R, 2.5 AL, 2.5 G

[56] References Cited
UNITED STATES PATENTS

| | | | |
|---|---|---|---|
| 260,069 | 6/1882 | Wallace............................. | 128/80 E |
| 1,058,322 | 4/1913 | Mueller............................. | 128/80 J |
| 1,381,290 | 6/1921 | Diadul, Jr. ........................ | 128/80 J |
| 1,656,322 | 1/1928 | Fischer.............................. | 128/80 J |
| 1,691,235 | 11/1928 | Fischer.............................. | 128/80 J |
| 3,713,231 | 1/1973 | Mochizuki....................... | 36/2.5 AL |
| 3,765,409 | 10/1973 | Merkle.............................. | 128/80 E |
| 3,861,067 | 1/1975 | Koyama et al. ................. | 36/2.5 AL |

Primary Examiner—John D. Yasko
Attorney, Agent, or Firm—Burns, Doane, Swecker & Mathis

[57] ABSTRACT

This invention relates to an orthopedic shoe that is useful in the treatment of club foot. The orthopedic shoe consists of a shoe and a calf support. The shoe and calf support are connected to one another in a manner that permits the shoe to move in relation to the calf support only about a horizontal axis that extends laterally through the ankle of the shoe.

7 Claims, 10 Drawing Figures

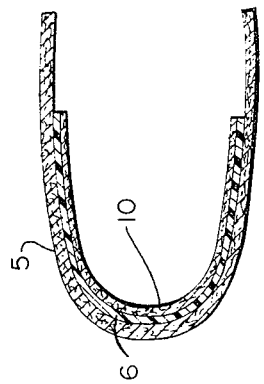
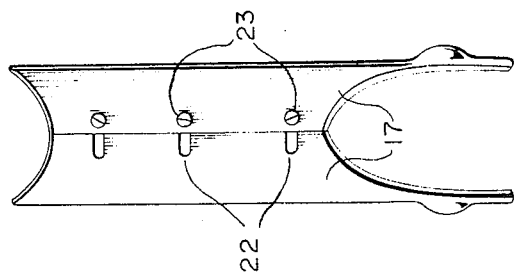
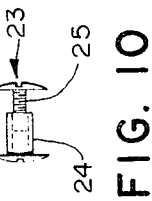
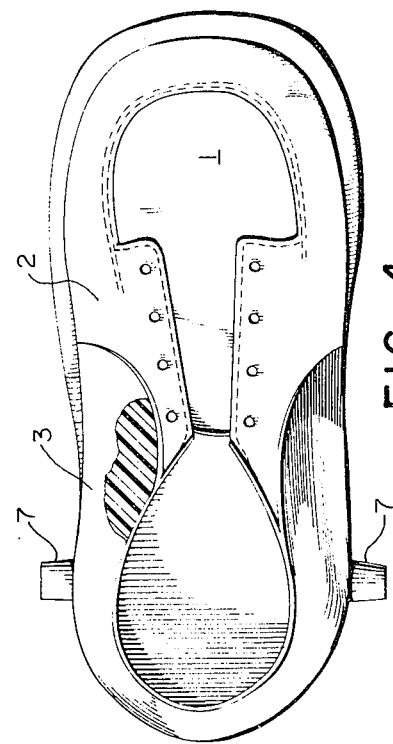
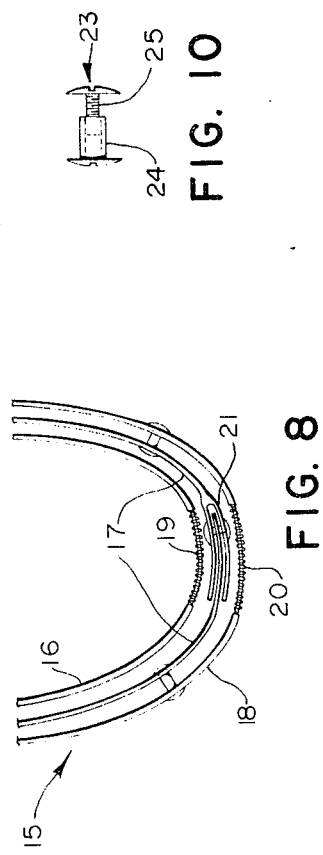

ORTHOPEDIC SHOE

This invention relates to an orthopedic shoe that is useful in the treatment of club foot.

In many instances of club foot, there is a tendency for the club foot to turn either inwardly or outwardly. This greatly hinders the ability of the person to walk correctly and easily. The person with the club foot can often walk more smoothly if the club foot can be prevented from turning to the side while maintaining flexibility in the foot.

SUMMARY OF THE INVENTION

My invention is directed to an orthopedic shoe that permits the club foot to have movement in an upwardly and downwardly direction in relation to the leg of that foot but does permit the foot to be turned inwardly or outwardly.

My orthopedic shoe consists of means such as a shoe that fits about the club foot and means such as a support that fits about the calf of the leg that has the club foot. The shoe and calf support are pivotally connected to one another at the ankle area along a horizontal axis that extends laterally through the ankle of the shoe. The pivotal axis of the shoe and calf support coincides with the horizontal lateral axis of movement of the foot. By having the shoe pivotally connected to the calf support at the ankle and in this manner, the person wearing the shoe and calf support can move the toe end of the foot upwardly and downwardly but cannot move the toe of the foot to either side. The shoe therefore permits movement of the toe of the foot in an upwardly and downwardly direction, which tends to let the wearer of the orthopedic shoe exercise and strengthen the muscles in the foot and encourage normal foot development and movement, but prevents movement of the toe of the foot in an inwardly or outwardly direction.

DRAWINGS

Figure 3:
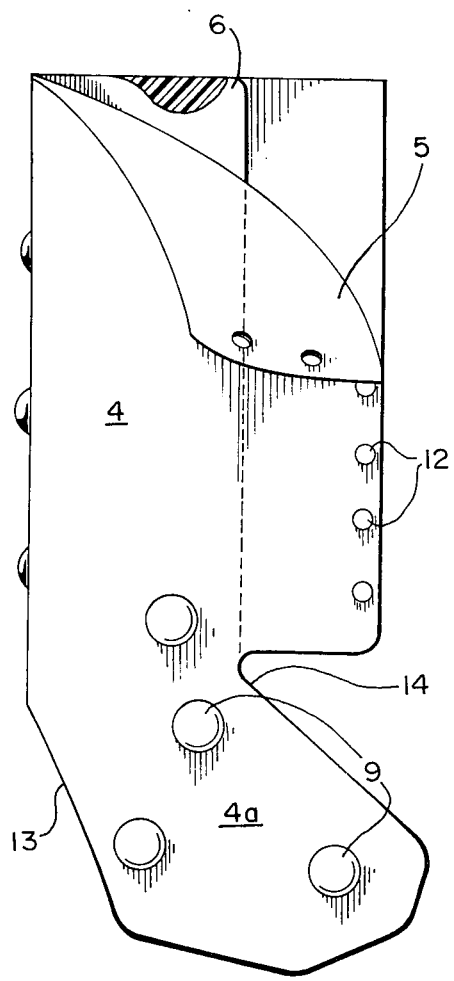
Figure 2:
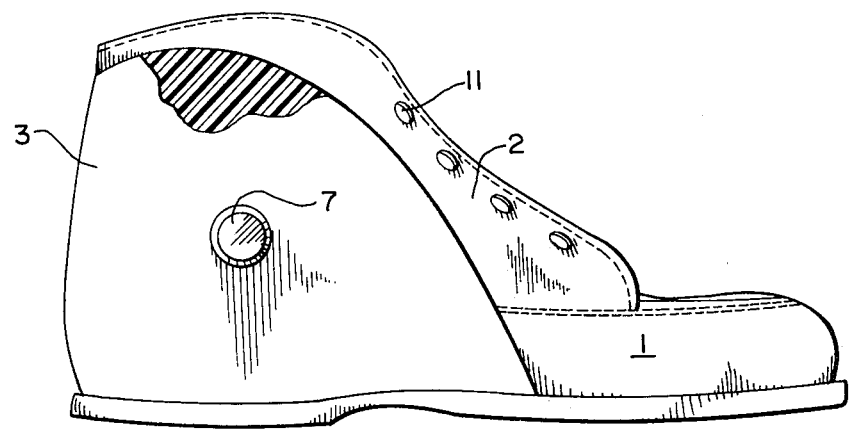
Figure 6:
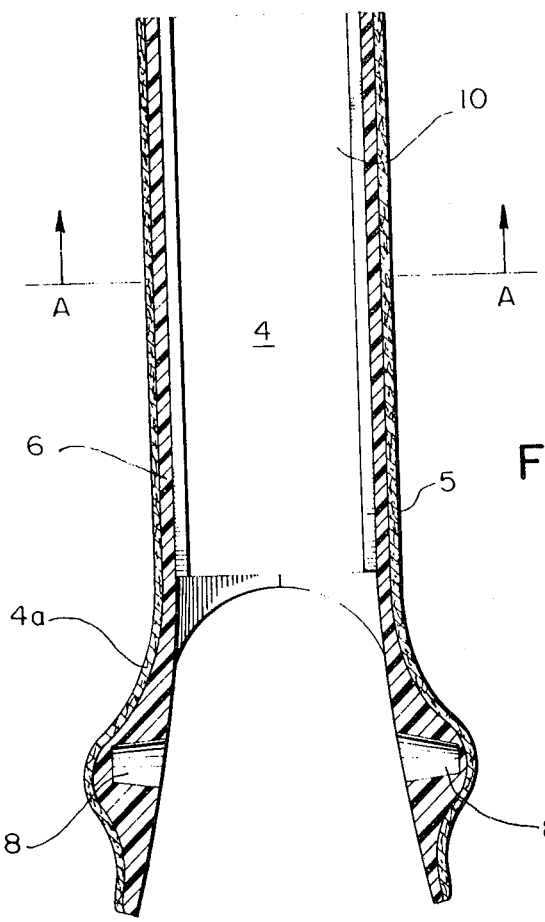
Figure 5:
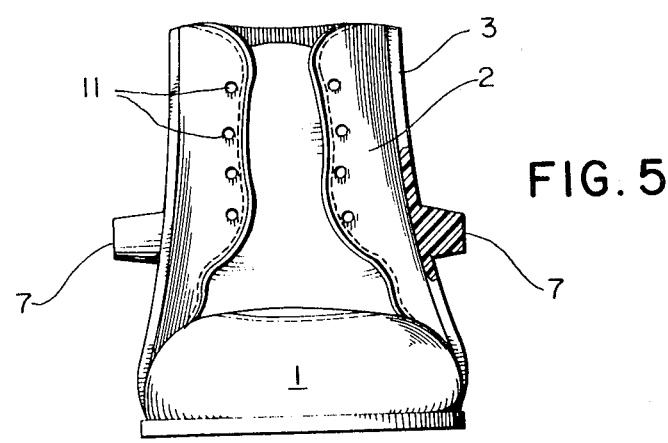

In the drawings:

FIG. 1 is a three-dimensional view of the shoe;
FIG. 2 is a side view of the shoe;
FIG. 3 is a side view of the calf support;
FIG. 4 is a top view of the shoe;
FIG. 5 is a front view of the shoe;
FIG. 6 is a front view of the calf support;
FIG. 7, shown with FIG. 4, is a section view of the calf support taken along section A—A of FIG. 6;
FIG. 8, shown with FIG. 4, is a section view of an adjustable calf support;
FIG. 9, shown with FIG. 4, is a rear view of the middle layer of an adjustable calf support; and
FIG. 10, shown with FIG. 4, is a detail of the construction of the bolt used in the adjustable calf support.

PREFERRED EMBODIMENT

The drawings illustrate a preferred embodiment of my orthopedic shoe. As shown in FIG. 1, the shoe consists of a conventional shoe 1 that is of ankle height and can be laced together at the top of the arch area 1a. As shown in FIG. 1, my orthopedic shoe also includes a calf support 4 which fits about the calf of the person afflicted with the club foot. The lower area 4a of the calf support is designed to fit over the ankle area of the shoe 1.

The shoe 1 is constructed of a layer 2 of suitable flexible material such as leather. As shown in FIGS. 2 and 4, the shoe 1 has overlaying the ankle and heel areas of the flexible layer 2 of the shoe 1, a shoe reinforcing layer 3. This shoe reinforcing layer 3 may be constructed of polyester and fiberglass in combination, or some other suitable relatively stiff material. The purpose of this shoe reinforcing layer 3 is to provide firm support about the ankle and heel areas of the wearer of the shoe 1.

The calf support 4 is also constructed using a layer 5 of suitable flexible material such as leather. As may be seen in FIGS. 3, 6 and 7, the calf support 4 has overlaying the inner side of the flexible layer 5 of the calf support, a calf support reinforcing layer 6. This calf support reinforcing layer 6 extends substantially from the bottom to the top of the calf support 4 along both sides and the back of the calf support 4. This calf support reinforcing layer 6 may be constructed of polyester resin and fibreglass in combination, or some other suitable relatively stiff material. The purpose of the calf support reinforcing layer 6 is to provide firm support about the calf and ankle areas of the wearer of the shoe 1 and calf support 4.

As may be seen in FIGS. 4 and 5, the shoe 1 has located on each side in the region of the ankle of the shoe 1, two protruding studs 7. These two protruding studs 7 are substantially cylindrical in shape and extend horizontally and laterally from each side of the shoe 1.

As may be seen in FIG. 6, the calf support 4 has located on the inside of the ankle area of the calf support 4a, on each side of the calf support 4, two sockets 8. These sockets 8 are hollowed out areas that are substantially cylindrical in shape and adapted to fit snuggly over the respective two studs 7 of the shoe 1.

The orthopedic shoe is assembled by positioning the two sockets 8 over the two respective studs 7. When assembled in this manner, the shoe 1 can pivot freely in relation to the calf support 4 along a horizontal axis extending laterally through the ankle of the shoe 1, but cannot pivot or move in any other direction such as sideways, or in a circular manner.

The two studs 7 and the two sockets 8 are positioned on the shoe 1 and ankle area of the calf support 4a respectively, such that the pivotal axis created by the studs 7 and superimposed sockets 8 coincides with the horizontal lateral axis about which the person moves the toe of the foot upwardly or downwardly in relation to the leg.

As may be seen in FIG. 3, flexible layer 5 of the calf support 4 is connected to the calf support reinforcing layer 6 at the ankle area of the calf support 4a by means of rivets 9. Other means of fastening the reinforcing layer 6 to the flexible layer 5 such as strong stitching or adhesive can be used in place of rivots. The rivots 9 help to reinforce the ankle area of the calf support 4a and to ensure that there is a good firm connection between the calf support 4 and the shoe 1.

For the purposes of comfort, as shown in FIG. 6, an inner pad 10 is located on the rear inside of the calf support 4. This inner pad 5 extends up the back and sides of the calf support 4 and is constructed of flexible leather, or some other soft material that improves the comfort characteristics of the calf support 4.

The upper front of the shoe is open in a conventional manner and can be fitted over the foot of the wearer and laced together by means of laces (not shown) and lace holes 11. The front of the calf support 4 is also open so that it can be fitted onto the wearer and laced together by means of laces and lace holes 12 that are located on each side of the calf support 4 close to the frontal opening. Other conventional means for closing such as buckles or snaps can be used.

To permit full pivotal movement between the shoe 1 and the calf support 4 about a horizontal lateral axis extending through the ankle, the lower rear area 13 and lower frontal area 14 of the calf support 4 are open so that when the shoe 1 and the calf support 4 are fitted together, the shoe 1 can pivot through a substantial distance about the studs 7 and sockets 8 without interfering with the body of the calf support 4. This lack of interference permits the wearer of the shoe to have complete freedom in moving the toe of the foot in an upwardly and downwardly direction in relation to the leg. However, because of the overall relatively rigid nature of the shoe 1, and the calf support 4, and the support provided when these two components are laced snuggly to the foot and calf respectively, the wearer of the shoe and calf support because only the horizontal lateral pivotal axis is built into the shoe, cannot move the foot in any direction other than upwardly and downwardly. This prevents the club foot from turning to the side.

The orthopedic shoe described herein can be modified from time to time to accommodate a child who is growing. The shoe 1 is interchangeable to fit larger sizes of foot. Moreover, the lace holes 12 and laces type construction at adjacently disposed front edges of the calf support 4 permit substantial latitude in the circumferential dimensions of the calf support 4, thus enabling the calf support to fit around a range of sizes of legs. To provide even greater latitude in the circumferential dimensions of the calf support 4, the back of the calf support 4 can be constructed of separate layers which are split vertically at the back, but not along the same vertical line. These overlapping layers can then be telescoped in association with one another to provide compressed or extended portions and thereby provide various circumferences which can be detachably fixed in position by means of hooks, snaps or the like.

A specific embodiment of a calf support 4 that can be adjusted to provide various circumferential dimensions is shown in FIGS. 8, 9 and 10. As can be seen from the section view shown in FIG. 8, the adjustable calf support 15 is constructed of four basic pieces, an inner pad 16, two interjoining reinforcing layers 17 and an outer flexible layer 18. The inner pad 16 and the outer flexible layer 18 each has an elastic central area (19 and 20 respectively) each of which can stretch or contract to accommodate various settings of the two interjoining reinforcing layers 17. As can be seen in FIG. 8, the two reinforcing layers 17 are constructed so that the edge of one layer fits into an overlapping edge section 21 of the other reinforcing layer. These two reinforcing layers 17 are secured together at a selected position by means of slots 22 and interacting bolts 23. The combination of the slots 22 and the bolts 23 permits the one reinforcing layer 17 to be set at various positions inside the overlapping section 21 so that the circumferential size of the overall calf support 15 can be adjusted to a wide range of settings.

A detail of the bolts 23 is shown in FIG. 10. One section of the bolt 23 is a thin head female section 24 and the other section is a thin head cooperating male section 25. Since the outer flexible layer 18 overlies and can cover the bolts 23, holes (not shown) can be cut in the outer flexible layer 18 at the positions where the bolts 23 are located so that the bolts can be loosened or tightened by a screw driver without having to remove the outer flexible layer 18. Rivets 26 can be used to provide a secure hold between the outer flexible layer 18 and the two reinforcing layers 17.

It should be kept in mind that the foregoing is a detailed description of a preferred embodiment of my invention, and that obvious design changes and modifications in materials and mechanical connections and construction can be made that still fall within the spirit of my invention. Accordingly, such modifications and changes are to be considered as being within the scope of my invention, as defined in the following claims.

The embodiments of the invention in which an exclusive property or privilege is claimed are defined as follows:

1. In an orthopedic device for the treatment of club foot comprising a relatively rigid foot holding means for holding the club foot and a relatively rigid calf holding means for holding the calf of the leg having said club food, said foot holding means and said calf holding means being connected to one another in a manner permitting the foot to move in relation to the calf only about a horizontal axis extending laterally relative to the ankle of the foot, the improvement wherein said calf holding means comprises:

a pair of vertically oriented calf support pieces that are curved to extend around portions of the calf;
each of said calf support pieces having spaced edges that are horizontally displaceable relative to adjacently disposed spaced edges of the other calf support piece;
first releasable connecting means for holding together two of said adjacently disposed edges of said calf support pieces, and
second releasable connecting means for holding the remaining two adjacently disposed edges of said calf support pieces in various relative positions of adjustment to adjust said calf holding means to different sizes of calf circumferences.

2. The orthopedic device of claim 1 wherein said first connecting means is arranged to hold together the associated edges in various positions of adjustment so as to provide adjustment of said calf holding means at two locations.

3. The orthopedic device of claim 1 wherein said first connecting means comprises one of laces, buckles, and snaps; said second connecting means being arranged to hold the adjacently disposed edges associated therewith in adjustable overlapping relation.

4. The orthopedic device of claim 1 wherein said remaining two edges of said calf support pieces overlap one another, and said second connecting means comprises at least one horizontally extending slot in one of said pieces in the region of the overlap, at least one corresponding hole in the other of the two pieces in the region of overlap so as to be alignable with said slot, and at least one tightenable member extending through an aligned hole and slot to hold said pieces together.

5. The orthopedic device of claim 1 wherein said calf holding means comprises three basic pieces, (1) an inner pad having a vertically extending elastic area therein which permits the circumferential dimension of the inner pad to be adjusted, (2) an outer layer having a vertically extending elastic area therein which permits the circumferential dimension of the outer layer to be adjusted, and (3) said calf support pieces positioned between the inner pad and outer layer, said pieces comprising interjoining layers overlapping one another and being detachably fastened to one another so that the total circumferential dimension of the two layers is adjustable.

6. The orthopedic device of claim 5 wherein said two interjoining layers are secured together by means of slots in one layer and interacting bolts in the other layer.

7. The device of claim 1 wherein said foot holding means is pivotally and detachably connected to said calf holding means by two protruding studs located on both outer sides of said foot holding means in the vicinity of an ankle portion thereof, and two corresponding stud receiving sockets located on both inner sides of a lower portion of said calf holding means.

* * * * *